United States Patent [19]

Vaillancourt

[11] 4,066,556

[45] Jan. 3, 1978

[54] FLUID FILTER AND METHOD OF MAKING SAME

[75] Inventor: Vincent Louis Vaillancourt, Livingston, N.J.

[73] Assignee: Johnson & Johnson, New Brunswick, N.J.

[21] Appl. No.: 736,670

[22] Filed: Oct. 28, 1976

[51] Int. Cl.$^2$ ............................................. C02C 1/14
[52] U.S. Cl. ............................... 210/448; 128/214 R; 210/454; 210/455; 210/500 M; 210/DIG. 23
[58] Field of Search ............... 210/435, 446, 448, 454, 210/455, 483, 484, 495, 500 M, 503, 505, 506, 508, DIG. 23; 128/214 R

[56] References Cited

U.S. PATENT DOCUMENTS

| | | | |
|---|---|---|---|
| 2,901,112 | 8/1959 | Naftulin et al. | 210/DIG. 23 |
| 2,914,181 | 11/1959 | Naftulin et al. | 210/DIG. 23 |
| 2,944,017 | 7/1960 | Cotton | 210/507 |
| 3,158,532 | 11/1964 | Pall et al. | 210/503 |
| 3,217,889 | 11/1965 | Berg | 128/214 R |
| 3,266,629 | 8/1966 | Megibow | 128/214 R |
| 3,543,940 | 12/1970 | Schmidt | 210/507 |
| 3,557,786 | 1/1971 | Barr et al. | 210/DIG. 23 |
| 3,583,460 | 6/1971 | Faust et al. | 128/214 R |
| 3,945,926 | 3/1976 | Kesting | 210/500 M |
| 3,949,744 | 4/1976 | Clarke | 128/214 R |

*Primary Examiner*—Frank W. Lutter
*Assistant Examiner*—Frank Sever
*Attorney, Agent, or Firm*—Richard J. Rodrick

[57] ABSTRACT

A fluid filter assembly is comprised of a flexible, compressible housing, a filter pouch in the housing formed from membrane filter media and having a fluid opening in one end thereof, a fluid inlet extending into the housing in fluid communication with the interior of the filter pouch through the fluid opening, and a fluid outlet extending from the housing in fluid communication with the interior of the housing external of the filter pouch. Fluid may pass through the fluid inlet into the interior of the filter pouch, then pass through the membrane filter media of the filter pouch into the interior of the housing external of the filter pouch and finally exit from the housing through the fluid outlet. The unique filter pouch may be made by providing a filter sheet of membrane filter media and folding the sheet substantially in half to form a filter pouch configuration having a folded edge, two edges adjacent the folded edge and an edge opposite the folded edge. The filter pouch may be incorporated into a filter assembly by enclosing the filter pouch in a flexible, compressible housing, sealing the adjacent edges of the filter pouch, providing a fluid inlet in the housing in fluid communication with the interior of the filter pouch and providing a fluid outlet in the housing in fluid communication with the interior of the housing external of the filter pouch.

10 Claims, 23 Drawing Figures

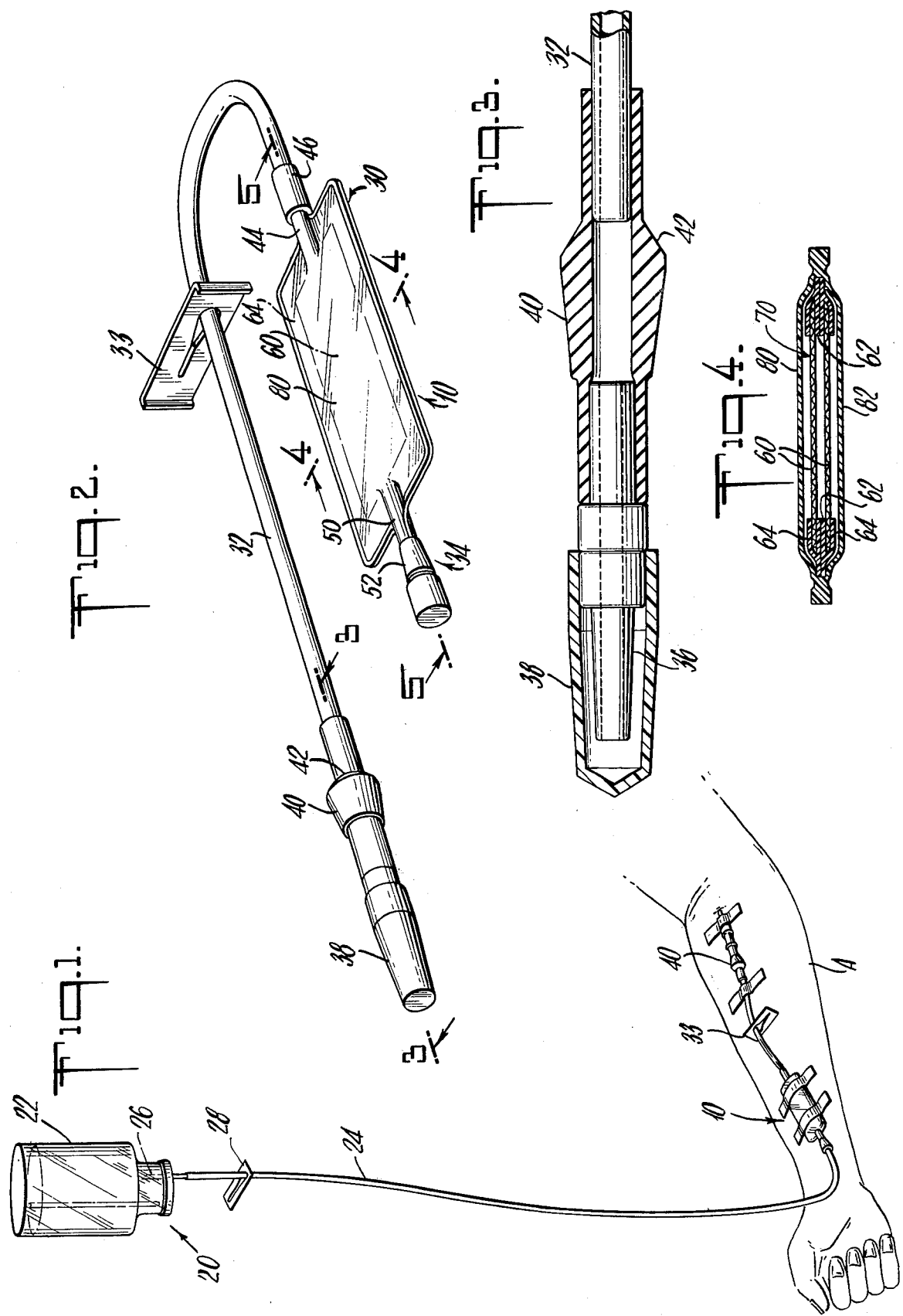

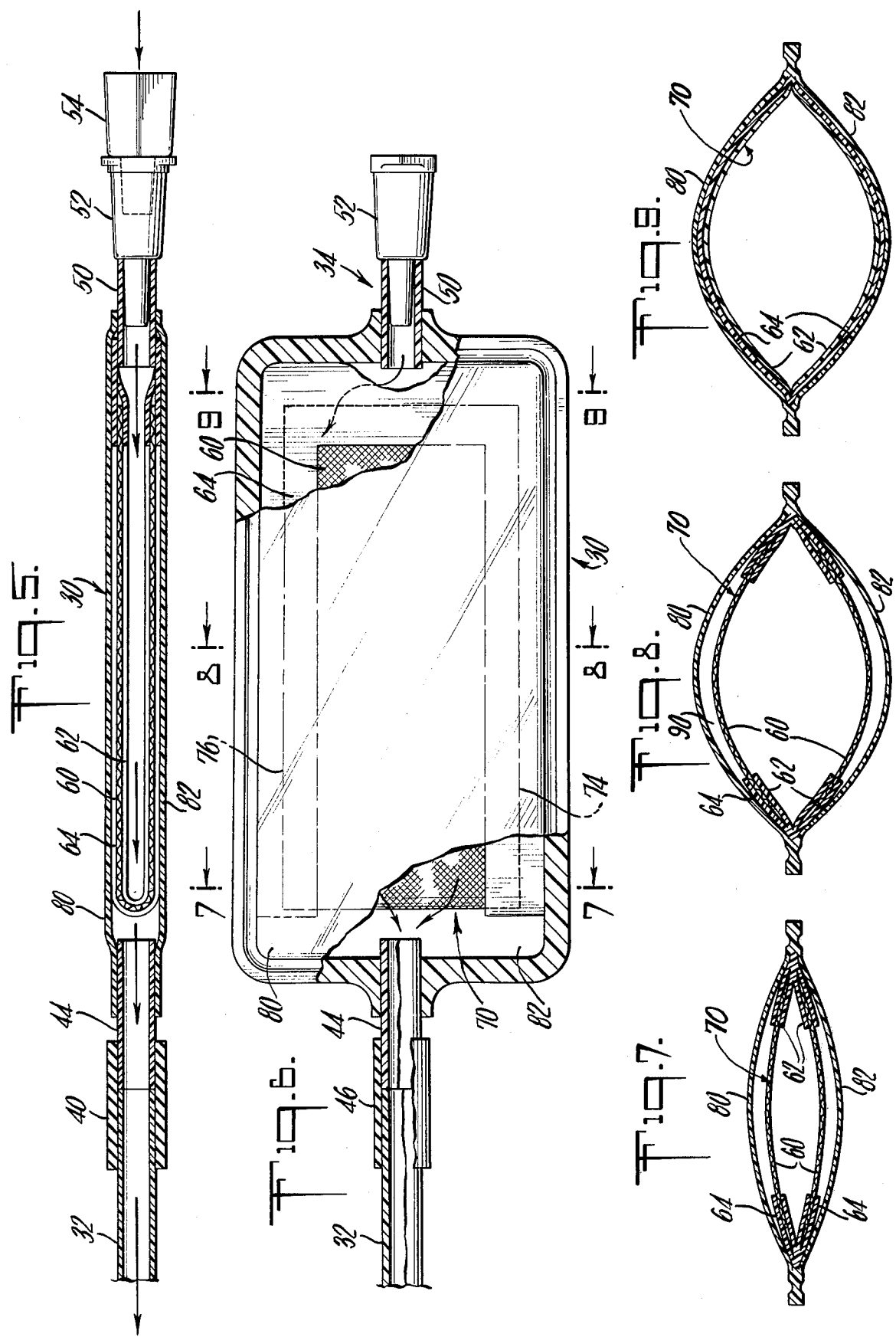

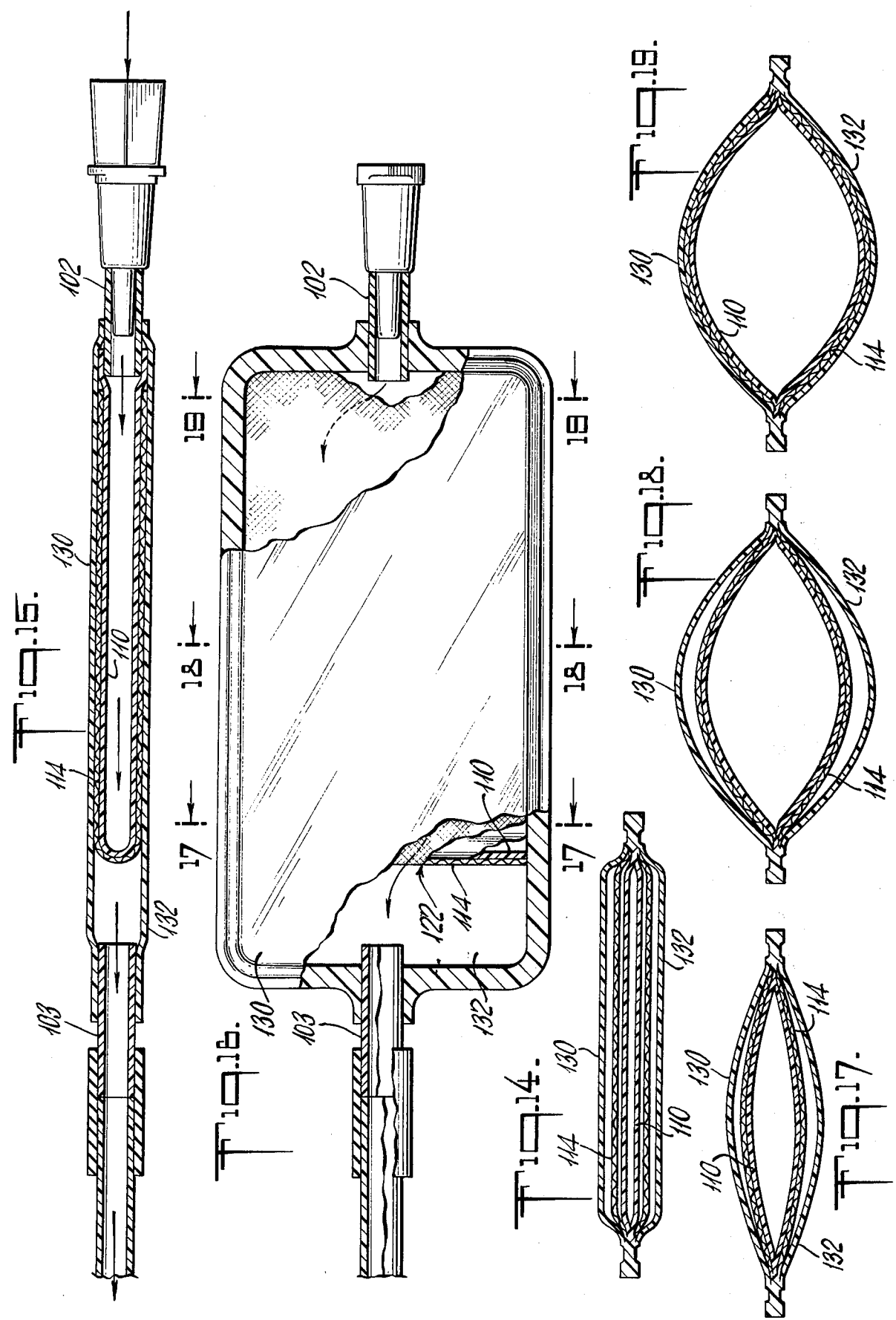

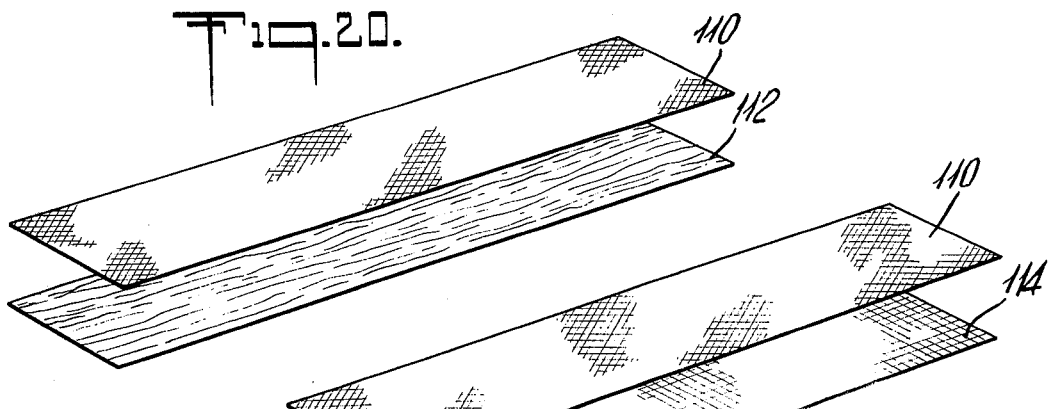
Fig.20.
Fig.21.
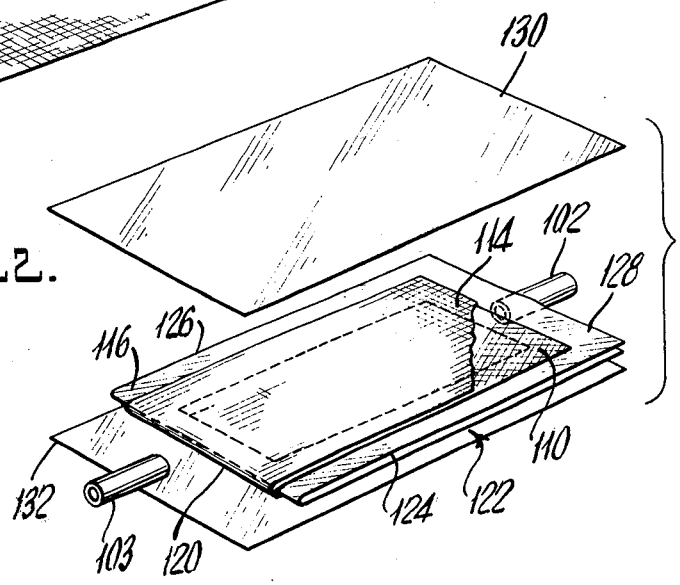
Fig.22.
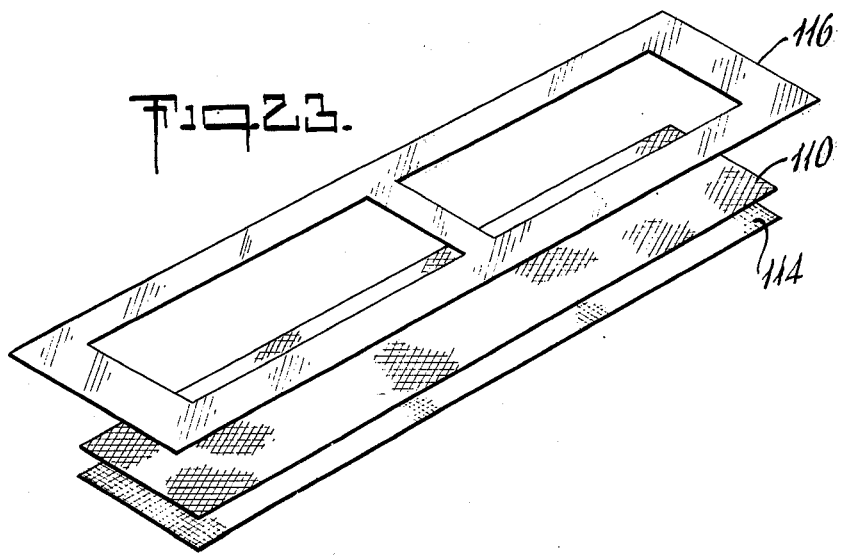
Fig.23.

FLUID FILTER AND METHOD OF MAKING SAME

BACKGROUND OF THE INVENTION

The present invention relates to a filter assembly and, more particularly, to a unique filter structure particularly useful in the filtering of parenteral fluids during the administration of such fluids. The invention further relates to methods for manufacturing the unique filter structure and the filter pouch embodiments usable therewith.

For some time it has been the preferred practice to filter intravenous and other parenteral solutions prior to the administration of such solutions to a patient to remove particulate matter that may be present in the solutions. Many different filter structures have been utilized for this purpose and many different procedures have been devised to insure that the fluids are properly filtered and administered with the highest degree of safety for the patient.

Recently, filter media have become commercially available that permit the filtration of intravenous fluids down to a particle size of 0.22 microns. This is significant in that a filter having this pore size effectively filters out all bacteria from the fluids in addition to removing particulate matter. Heretofore, one of the main drawbacks of utilizing a 0.22 micron filter was that a very high pressure drop was created by the presence of the filter, thus, necessitating the use of a pump to sufficiently overcome the back pressure. Also, the 0.22 micron membrane filter media that have been found to be particularly applicable for use in the filtering of intravenous fluids are exceptionally difficult to handle during the fabrication of the filter media into appropriate filter structures. This is true because most of such filter media have very low tear strengths and do not form adequate heat seals with other plastic materials. Therefore, the geometrical configurations heretofore available with the 0.22 micron membrane filter media have been relatively flat surfaces which greatly limit, because of size considerations, the available filter area for the passage of fluids. Thus, the problem of excessive back pressure is increased because of the relatively small filtering surfaces.

Another problem encountered in the use of prior filters was that of air blockage due to improper priming. Since the type of filters contemplated by this invention are hydrophilic, they do not pass air and, consequently, air accumulates at the filter surface and reduces the available filtration area. The result of this air accumulation at the filter surface is that it reduces the flow rate and contributes to the malfunction of the system. A significant portion of this problem may be overcome by priming the filter assembly prior to its use; however, since all prior filters have been constructed from relatively rigid housing materials, this priming technique has been relatively complicated and has not always been effective in removing all of the air from the filter housing.

It will be apparent from the foregoing discussion that many significant problems have existed in prior attempts to manufacture and use a filter assembly to provide absolute filtration of intravenous and other fluids. These problems are in part occasioned by the difficulty in handling the presently available membrane filter media and by the relatively rigid housing structures that have been heretofore utilized.

SUMMARY OF THE INVENTION

The present invention provides a unique filter assembly for use in the filtering of intravenous and other fluids which can provide absolute (0.22 microns) filtration of the fluids without the use of pumps, or other mechanical assists, and without the necessity of utilizing a complicated priming system prior to the use of the filter. These results are accomplished by providing a unique filter pouch which is constructed from an appropriate membrane filter material and fabricated in such a manner that the filter pouch may be securely and effectively incorporated into a filter assembly.

The filter assembly preferably comprises a flexible compressible housing which encloses the filter pouch. A fluid inlet extends into the housing in fluid communication with the interior of the filter pouch and a fluid outlet extends from the housing in fluid communication with the interior of the housing external of the filter pouch. By providing the membrane filter media in a pouch configuration, a larger amount of filter surface area is available than previously experienced with prior filter assemblies. This, of course, will not only improve the flow rate characteristics of the filter but will also obviate the necessity for utilizing a pump, or other mechanical means, to force the fluid through the filter.

With the above filter structure, the intravenous fluid may pass through the fluid inlet into the interior of the filter pouch, then pass through the membrane filter media of the filter pouch into the interior of the housing external of the filter pouch and finally exit from the housing through the fluid outlet. Priming of this unique filter assembly prior to patient hook-up is easily accomplished because the filter is made in a compressed configuration and, therefore, initially contains essentially no internal air volume. Since the filter assembly does not expand until the fluid has entered the filter pouch, the possibility of air entrapment on either the upstream or downstream sides of the filter media is virtually eliminated. As mentioned above, prior filter assemblies usable with a 0.22 micron membrane filter material were constructed of relatively rigid materials and, therefore, were incapable of being primed in the above-described manner.

The unique filter pouch of the present invention may be made by providing a filter sheet of membrane filter media, sealing the filter sheet around its periphery to a flexible reinforcing structure to form a unitary assembly having a substantial surface area of the filter sheet exposed and folding the unitary assembly substantially in half to form a filter pouch configuration having a folded edge, two edges adjacent the folded edge and an edge opposite the folded edge. The filter pouch may then be incorporated into a filter assembly by enclosing the filter pouch in a flexible, compressible housing, sealing the adjacent edges of the filter pouch, providing a fluid inlet in the housing in fluid communication with the interior of the filter pouch and providing a fluid outlet in the housing in fluid communication with the interior of the housing external of the filter pouch.

In a preferred embodiment of the invention, the filter pouch is formed from a porous polycarbonate film. This specific filter material provides certain advantages over other filter media usable with this invention in that (1) possesses superior heat-sealing properties, (2) does not swell in the presence of dextrose and other parenteral solutions (swelling of filter media can result in loss of flow rate over a period of time), (3) contains no extractables, such as, surfactants, plasticizers, residual solvents, etc. and (4) has very low moisture sensitivity.

BRIEF DESCRIPTION OF THE DRAWINGS

FIG. 1 is a perspective view illustrating the unique filter assembly of the present invention in place during the administration of intravenous fluids into a patient;

FIG. 2 is a perspective view illustrating the entire filter assembly of one embodiment of the present invention;

FIG. 3 is a cross sectional view taken along line 3—3 in FIG. 2;

FIG. 4 is a cross sectional view taken along line 4—4 in FIG. 2;

FIG. 5 is a cross sectional view taken along line 5—5 in FIG. 2;

FIG. 6 is a plan view of one embodiment of the filter assembly with portions broken away to illustrate internal structure and fluid flow;

FIG. 7 is a cross sectional view taken along line 7—7 in FIG. 6;

FIG. 8 is a cross sectional view taken along line 8—8 in FIG. 6;

FIG. 9 is a cross sectional view taken along line 9—9 in FIG. 6;

FIG. 14 is a cross sectional view taken along line 14—14 in FIG. 13;

FIG. 15 is a cross sectional view taken along line 15—15 in FIG. 13;

FIG. 16 is a plan view of the embodiment of FIG. 13 with portions broken away to illustrate internal structure and fluid flow;

FIG. 17 is a cross sectional view taken along line 17—17 in FIG. 16;

FIG. 18 is a cross sectional view taken along line 18—18 in FIG. 16;

FIG. 19 is a cross sectional view taken along line 19—19 in FIG. 16;

FIG. 20 is a perspective view illustrating components of another embodiment of the unique filter pouch of the present invention prior to assembly of such components;

FIG. 21 is a perspective view illustrating other embodiment components;

FIG. 22 is a further perspective view illustrating the fabrication of the filter assembly; and FIG. 23 is a perspective view illustrating still another embodiment of certain components of the present invention.

DESCRIPTION OF THE PREFERRED EMBODIMENTS

Figure 10:
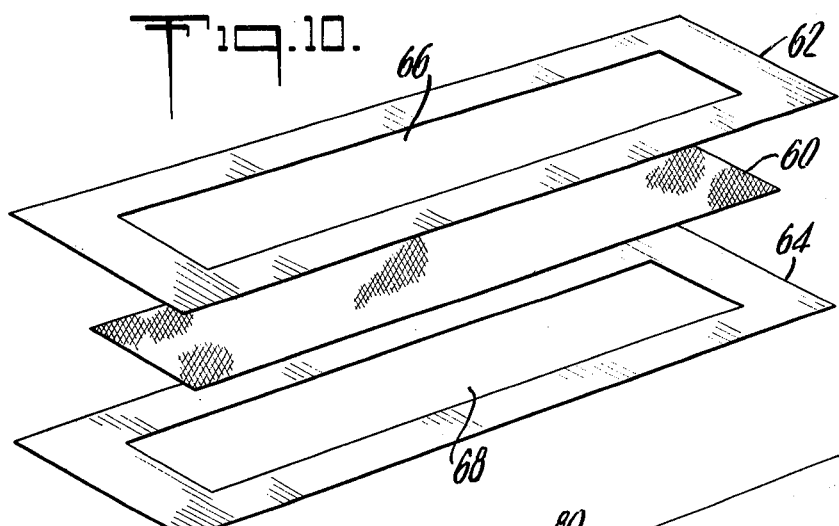
FIG. 10 is a perspective view illustrating components of one embodiment of the unique filter pouch of the present invention prior to assembly of such components.

Referring to FIG. 1, one embodiment of the filter assembly of the present invention is illustrated generally at numeral 10 attached to the arm A of a patient during the administration of an intravenous fluid which is fed to the patient from an administration set shown generally at 20. Administration set 20 comprises an intravenous solution container 22 which may be in the form of a glass bottle, plastic bag or other suitable means, and is preferably suspended approximately 2 to 3 feet above the administration site. A length of tubing 24 having a spike 26 at the upper end thereof for penetrating the closure of intravenous solution container 22 extends downwardly from the container and delivers the intravenous fluid to filter assembly 10. A clamp 28 may be provided in the tubing 24 to control the flow of fluid therethrough. Also, appropriate flow control devices, such as, drip chambers or other fluid control apparatus, may be associated with tubing 24, if desirable. This equipment is well known in the art of administering intravenous solutions and will not be described in further detail herein.

Referring to FIG. 2, filter assembly 10 is illustrated in detail and is shown to have a flexible, compressible housing 30, a length of extension tubing 32 extending from one end of housing 30 and a connector 34 attached to the other end of housing 30. Tubing 32 is adapted to be connected to a conventional intravenous catheter assembly and to deliver filtered intravenous fluid from the downstream (distal) end of housing 30 to the intravenous catheter and, thus, into the vein of a patient. A suitable clamp 33 may be provided to control the flow of fluid through the tubing 32. The free end of tubing 32 is described in detail in FIG. 3. A connector 36 is attached to the end of tubing 32 and is equipped with a male fitting that is adapted to be received into a female fitting on an intravenous catheter. A cap 38 is positioned over connector 36 to protect and preserve the sterility of the connector. Of course, cap 38 must be removed from connector 36 prior to the attachment of the connector to the intravenous catheter and is also removed or loosened during priming to permit air to be eliminated from the system. Connector 36 is attached in fluid communication to the end of tubing 32 by a fitting 40 which is preferably made of natural rubber, or a similar elastomer, which may be utilized as an injection site for injecting medicaments or other fluids into the system. This injection is preferably accomplished by inserting the needle of a syringe or other device into the tapered annular shoulder 42 provided on the fitting.

Referring to FIG. 6, a fluid outlet formed by a relatively short length of tubing 44 is provided in the downstream, distal end of housing 30 and tubing 32 is connected to tubing 44 by a sleeve 46 positioned over the mating ends of each of said pieces of tubing. A heat seal or other appropriate attachment may be utilized to facilitate bonding of these three elements together. The upstream, or proximal, end of housing 30 is also provided with a relatively short length of tubing 50 which provides a fluid inlet into housing 30 for the intravenous solution supplied by container 22. A female fitting 52 is secured in the proximal end of tubing 50 and is adapted to be connected to a male fitting on the distal end of tubing 24. A cap 54 is positioned in the proximal end of fitting 52 to preserve sterility of the system and to protect the fitting as more clearly illustrated in FIG. 5. Of course, cap 54 must be removed from fitting 52 prior to the connection of tubing 24 thereto.

The unique filter pouch and housing of one embodiment of this invention, and the method of making and fabricating these components, will now be described in detail. As previously stated, the filter media contemplated for use with the present invention are membrane-type materials that have the capability of filtering particles and bacteria having a size down to 0.22 microns. The presently available commercial material usable in this type of application is extremely difficult to handle and to fabricate. For example, it has been found that most available membrane filter media of this type have a common problem with regard to sealing, that is, the filter media do not lend themselves to conventional sealing techniques, such as, heat sealing, solvent sealing, ultrasonic sealing, etc. To overcome these drawbacks, one aspect of the present invention is to provide a unique procedure for supporting this type membrane filter media and for fabricating it in a pouch configuration into the filter housing.

Referring to FIG. 10, a filter sheet 60 of membrane filter media is shown positioned between an upper frame member 62 and a lower frame member 64. Although many membrane filter media are usable with the present invention, one of the preferred materials is a membrane formed from mixed esters of cellulose reinforced with a polyester mesh. One such membrane filter media is manufactured by the Gelman Instrument Company and marketed under the trademark Tuffryn-200. This material has a pore size of 0.2 micron and a thickness of approximately 130 microns.

Frame members 62 and 64 have rectangular dimensions slightly larger than filter sheet 60 and are provided with rectangular central openings 66 and 68, respectively, which, when positioned adjacent filter sheet 60, provide a substantial exposed central surface area on both sides of the filter sheet. Frames 62 and 64 may be formed from any suitable plastic material with the presently preferred material being polyvinyl chloride having a preferred thickness of approximately 2 mils. The configuration of the filter pouch is accomplished by placing filter sheet 60 into intimate contact with frame members 62 and 64 and heat sealing the 3-component assembly together around the outer periphery of the filter sheet.

Figure 11:
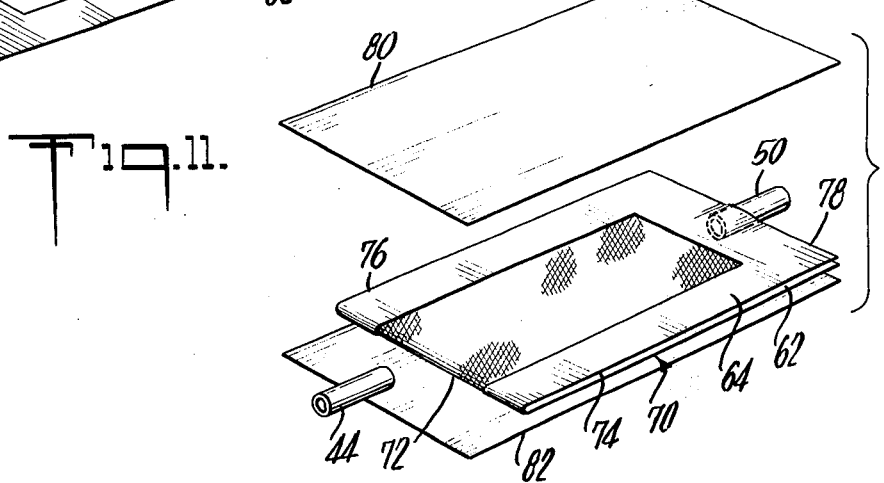
FIG. 11 is a further perspective view illustrating the fabrication of the filter assembly.

Referring to FIG. 11, the unitary assembly formed by filter sheet 60 and frame members 62 and 64 is shown folded substantially in half to form a filter pouch 70 having a folded edge 72, two edges 74 and 76 adjacent the folded edge and an edge 78 opposite the folded edge. The completion of the filter assembly is accomplished by enclosing filter pouch 70 within a flexible, compressible housing formed by two flexible plastic sheets 80 and 82. Plastic sheets 80 and 82 are preferably heat-sealed to filter pouch 70 along adjacent edges 74 and 76 external of filter sheet 60. Concurrent with this heat sealing operation, tubing 44 and 50 are sealed between sheets 80 and 82 to provide the fluid inlet and fluid outlet for the filter assembly.

Figure 12:
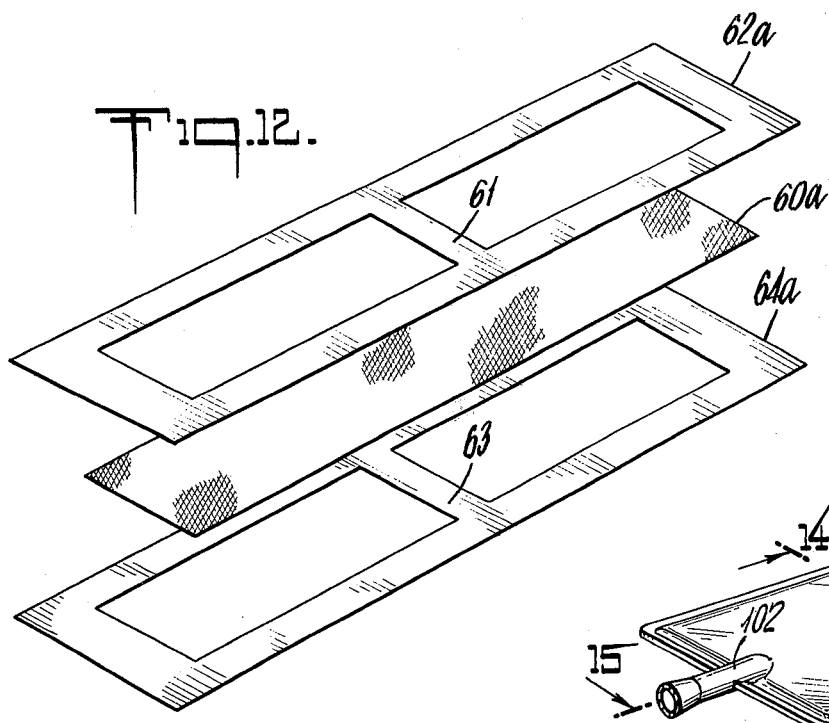
FIG. 12 is another perspective view illustrating another embodiment of the fabrication of certain components of the present invention.

FIG. 12 illustrates a further embodiment of the present invention wherein a filter sheet 60a is positioned between an upper frame 62a and a lower frame 64a. The only structural distinction between this embodiment and the embodiment illustrated in FIG. 10 is the addition of support elements 61 and 63 extending across the central portion of frames 62a and 64a, respectively. Supports 61 and 63 add additional support to the unitary assembly when it is eventually folded into the filter pouch structure as illustrated in FIG. 11. It should be noted, however, that a substantial filter area still remains on both sides of filter sheet 60a.

The final structure of this embodiment of the filter assembly is illustrated in detail in FIGS. 5 and 6. Filter sheet 60 is shown sealed around its outer periphery to frame member 64 which, in turn, is sealed along its adjacent edges between outer plastic sheets 80 and 82 which form the housing for the filter assembly. In the illustrated embodiment, the seal between plastic sheets 80 and 82 is formed outwardly from the edges of filter sheet 60; however, if desired, a single seal may be utilized to join all of the components of the filter assembly together. For example, the seal between plastic sheets 80 and 82 could be formed directly over the outer edges of filter sheet 60 to thereby accomplish a sealing procedure joining all elements of the filter assembly with a unitary seal. It should be noted that the fluid inlet formed by tube 50 in the proximal end of housing 30 is in fluid communication with the end of filter pouch 70 opposite to the folded end. Since this end has not been sealed, it forms a fluid opening to permit fluids to pass through the fluid inlet into the interior of the filter pouch. The intravenous fluid can then pass through the membrane filter media of filter pouch 70 into the interior of housing 30 at a location external from the filter pouch. Referring to FIGS. 5 and 6, the direction of fluid flow is illustrated by the arrows which show the fluid entering through tube 50, passing into the interior of filter pouch 70, passing through the filter pouch into the interior of housing 30 external of the pouch and then exiting from the housing through tube 44 formed in the distal end of the housing.

The cross sectional configuration of the filter assembly during the passage of fluid therethrough is illustrated in FIGS. 7 to 9. In FIG. 9, a location proximal to the fluid opening in filter pouch 70 is illustrated in an expanded condition with frame members 62 and 64 in contact with the outer plastic sheets 80 and 82. As the fluid flows into the fluid opening of filter pouch 70, the pouch expands as illustrated in FIG. 8 and the fluid passes through the membrane filter media and into the interior of housing 30 external from the filter pouch. The FIG. 8 cross sectional view illustrates the spacing 90 that exists as a result of the unique attachment between plastic sheets 80 and 82 and the frame members 62 and 64. Since filter sheet 60 is attached inwardly from the seal between the plastic sheets and the frame members, the less extensible membrane filter media will expand less under the pressure of the intravenous fluid than plastic sheets 80 and 82 and thus create a space into which the fluid may flow. In addition, of course, the fluid is also free to flow through the filter pouch at the folded end of filter sheet 60 adjacent tubing 44. As previously stated, however, this structural attachment of the filter sheet to the housing is not critical to the subject invention in that it has been found that the degree of flow required for operation of a filter of the type contemplated herein will also adequately function when the filter sheet is attached in other manners.

Referring to FIG. 4, the filter assembly is illustrated in a relaxed condition prior to the entry of fluid therein. It will be noted that the outer plastic sheets 80 and 82 are substantially planar and are positioned adjacent filter sheet 60 of filter pouch 70. As previously stated, one aspect of the present invention is the self-priming feature of the unique filter assembly. Prior to the initiation of intravenous fluid flow into the patient, the filter assembly may be virtually entirely purged of air because of the compressed condition of the outer plastic sheets 80 and 82 which, in turn, compress filter pouch 70 and substantially eliminates any dead air spaces that may exist in the filter assembly. This, of course, is an important advantage over prior intravenous fluid filters that have utilized rigid housings in combination with the absolute filter material.

Although all of the materials utilized in the construction of the filter assembly of the present invention are not critical, it will be appreciated that the materials should preferably be bio-compatible and that, in order to facilitate fabrication of the filter assembly, most of the materials should preferably be heat-sealable. By way of example, the outer plastic sheets 80 and 82 are preferably formed from polyvinyl chloride having a thickness of 8 mils. Likewise, all of the tubing, including tubing 32, 44 and 50, are preferably constructed of polyvinyl chloride.

The size of filter pouch 70 and housing 30 are not critical; however, it has been found that the overall dimensions should be limited in order to conveniently position the filter assembly on the arm of a patient but at the same time provide the superior flow rates achievable with this unique filter structure. The presently preferred outside dimensions for housing 30 are 2 inches from the distal to the proximal end and 1¼ inches wide.

One preferred embodiment of the present invention contemplates the use of a unique membrane filter material which has certain properties that are superior to the properties of other filter media usable with the invention. This unique membrane filter material is a polycarbonate film which is available from the Nuclepore Corportion and is made in accordance with that company's unique manufacturing process. The material is marketed under the trade name "Nuclepore". The polycarbonate membrane is unique as a filter media for the subject invention because of its following properties:

1. The polycarbonate membrane possesses heat-sealing properties which are superior to the properties of other membrane filter media which are commercially available and adaptable for use with the present invention. This, of course, enables the membrane to be handled in a manner different from that of the other filter media.

2. The polycarbonate film has been found to be extremely stable and does not swell in the presence of dextrose and other parenteral solutions. This is an advantage in that swelling of the filter media in the presence of these solutions can result in loss of flow over a period of time.

3. The polycarbonate film contains no undesirable extractables, such as, surfactants, plasticizers, residual solvents, etc., and 4. The unique membrane has a very low moisture sensitivity.

The polycarbonate membranes are manufactured in accordance with a unique two-step manufacturing process. In accordance with this process, a polycarbonate film is first exposed to collinated, charged particles in a nuclear reactor. As the particles pass through the material, they leave sensitized tracks. The pore density (pores/cm$^2$) is controlled by the residence time in the irradiator. In the second step of the manufacturing process, the tracks left by the charged particles in the reactor are preferentially etched into uniform, cylindrical pores. By controlling the length of the etching process, a specified pore size is produced. In its preferred condition, the pore size of this polycarbonate film is about 0.2 microns, and the thickness of the film is about 10 microns.

Because the polycarbonate membrane has been found to have heat-sealing properties which are superior to the properties of the other filter media usable with the present invention, a slightly different process for fabricating the unique filter assembly of the present invention utilizing the polycarbonate membrane has been devised. This process and the unique filter assembly structure formed thereby will now be described in detail.

Figure 13:
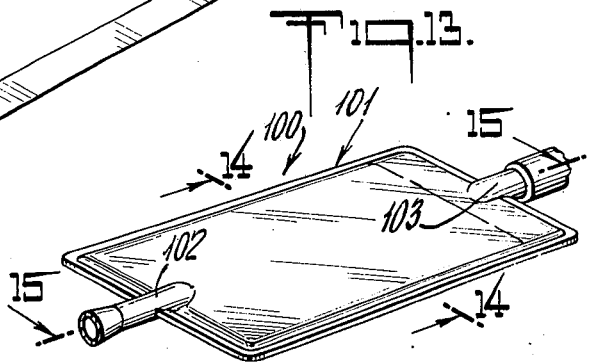
FIG. 13 is a perspective view illustrating the filter assembly of another embodiment of the invention.

Referring to FIG. 13, the filter assembly 100 is partially illustrated and is shown to have a flexible, compressible housing 101 with an inlet tubing 102 and an outlet tubing 103 extending from opposite ends thereof. Although filter assembly 100 is intended to be essentially identical to filter assembly 10 illustrated in FIG. 2, except for the internal configuration of housing 101, the remaining tubing and fittings have been deleted for convenience.

Referring to FIG. 20, a filter sheet 110 of the unique polycarbonate film is illustrated positioned adjacent a sheet of reinforcing material 112. Because the polycarbonate film possesses a relatively low burst strength in this application of the film, it has been found to be desirable to provide a reinforcing, or support, layer over substantially the entire outer surface area of the film to prevent rupture, or other failure, of the film during use. Support layer 112 selected for the FIG. 20 embodiment is a white nonapertured nonwoven fabric composed of cellulosic wood pulp and polyester fibers bonded overall with a resin adhesive. This support material has been found to effectively support the polycarbonate membrane without substantially affecting the flow rate when normal pressures are utilized during the administration of intravenous fluids. The support material is a commercial product of the Chicopee Manufacturing Company and is available under their Customer Product Specification Number 04-076.

FIG. 21 illustrates an alternative support layer 114 which has also been found to very effective for supporting polycarbonate film 110 during its normal use as an intravenous fluid filter. Support material 114 is a polyvinyl chloride scrim formed with substantially the same rectangular dimensions as polycarbonate film 110. This support material has been found to provide effective support for the film without substantially affecting the flow rate of the filter.

Referring to FIG. 23, it will be seen that polycarbonate film 110 and support material 114 have a frame member 116 disposed thereover. Frame 116 may be essentially identical to frames 62 and 64 which are illustrated in FIG. 10, but preferably has a central support member such as that shown on frames 62a and 64a in FIG. 12. The use of frame 116 has been found to be useful in some instances when it is desirable to test the efficacy of the seal and the burst strength of membrane 110 prior to the incorporation of the filter pouch into a filter assembly and it also contributes to the formation of the heat-seals during the fabrication of the filter assembly. The formation of a filter pouch utilizing frame 116 is illustrated in FIG. 22 wherein the three-piece composite illustrated in FIG. 23 has been folded substantially in half along a fold line 120 to form a filter pouch 122 having folded edge 120, two edges 124 and 126 adjacent the folded edge and an edge 128 opposite the folded edge.

The completion of the filter assembly is accomplished by enclosing filter pouch 122 within a flexible, compressible housing formed by two flexible plastic sheets 130 and 132. Plastic sheets 130 and 132 are preferably heat-sealed to filter pouch 122 along adjacent edges 124 and 126. Concurrently with this heat-sealing operation, tubing 102 and 103 are sealed between sheets 130 and 132 to provide the fluid inlet and fluid outlet, respectively, for the filter assembly. This phase of the fabricating procedure is essentially identical to that illustrated and described in connection with the embodiments of the prior figures. Of course, the primary difference between this embodiment and the previously described embodiments is the addition of support layer 114 which may be either freely positioned within the filter assembly or heat sealed either at selected portions or completely around its periphery to the remainder of the filter pouch.

The final structure of this embodiment of the filter assembly of the present invention, without the frame member 116 included therein, is illustrated in detail in FIGS. 15 and 16. Filter sheet 110 and support material 114 are shown folded substantially in half and sealed along their adjacent edges to the flexible plastic sheets 130 and 132 which form the housing for the filter assembly. The fluid inlet formed by tube 102 in the proximal end of housing 101 is in fluid communication with the end of filter pouch 122 opposite to the folded end. Since this end has not been sealed, it forms a fluid opening to permit fluids to pass through the fluid inlet into the interior of the filter pouch. The intravenous, or other, fluid can then pass through the polycarbonate membrane and support material 114 of filter pouch 122 into the interior of housing 101 at a location external from the filter pouch. Referring to FIGS. 15 and 16, the direction of fluid flow is illustrated by the arrows which show the fluid entering through tube 102, passing into the interior of filter pouch 122, passing through the filter pouch into the interior of housing 101 external of the pouch and then exiting from the housing through tube 103 formed in the distal end of the housing.

FIGS. 17 to 19 depict the cross sectional configuration of the filter assembly during the passage of fluid therethrough. It will be apparent that the location of support material 114 on the external surface of membrane 110 lends support and reinforcement to the membrane and avoids excessive distortion and, therefore, possible failure of the membrane.

Referring to FIG. 14, the filter assembly is illustrated in a relaxed condition prior to the entry of fluid therein. As in the case of the FIG. 4 embodiment, the outer plastic sheets 130 and 132 are substantially planar and are positioned adjacent support material 114 of filter pouch 122.

It will be apparent from the foregoing description that the present invention provides a unique filter assembly which has many advantages over filter assemblies previously utilized in the absolute filtration of intravenous and other fluids. This unique filter assembly insures superior flow rate through a 0.22 micron membrane filter media without the assistance of pumps, or other mechanical devices. The filter assembly also provides a flexible, compressible housing and filter pouch construction that facilitates priming of the assembly in a manner that is more efficient and more effective than prior filters.

The present invention also provides unique methods for making filter pouches from membrane filter media and for incorporating the unique filter pouches into filter assemblies.

What is claimed is:

1. A filter assembly of a conventional size convenient for positioning on the arm of a patient, and for use in the filtering of intravenous fluids, comprising: a housing; a flexible filter pouch in said housing formed from porous membrane filter media having a pore size not greater than 0.22 microns, said pouch having a fluid opening in one end thereof; fluid inlet means extending into said housing in fluid communication with the interior of said filter pouch through said fluid opening; and fluid outlet means extending from said housing in fluid communication with the interior of said housing external of said filter pouch; whereby fluid may pass through said fluid inlet means into the interior of said filter pouch, pass through the membrane filter media of said filter pouch into the interior of said housing external of said filter pouch and then exit from said housing through said fluid outlet means, said filter pouch providing a sufficiently low pressure drop thereacross, so as to eliminate the requirement of a fluid pump to force said fluid through said assembly.

2. The filter assembly of claim 1, wherein said membrane filter media comprises a porous polycarbonate film.

3. A filter assembly of a conventional size convenient for positioning on the arm of a patient, and for use in the filtering of intravenous fluids during the administration of such fluids comprising: a substantially planar housing comprising: a pair of flexible sheets sealed together around their peripheries; a flexible filter pouch in said housing formed from porous membrane filter media having a pore size not greater than 0.22 microns, said pouch comprising a first flexible frame member sealed around its periphery to one side of said filter membrane and a second flexible frame member sealed around its periphery to the other side of said filter membrane, each frame members having at least one opening therein exposing a substantial surface area of said filter membrane, said filter membrane and said frame members being folded substantially in half and having seal means along two edges adjacent the folded edge so that the edge of said pouch opposite said folded edge defines a fluid opening in said pouch, said folded pouch providing a sufficiently low pressure drop thereacross, so as to eliminate the requirement of a fluid pump to force said fluids through said assembly, said flexible sheets of said housing adapted to be compressed together with said flexible pouch therebetween for facilitating the priming of the filter assembly to substantially eliminate any air space within said housing; fluid inlet means extending into said housing in fluid communication with the interior of said filter pouch through said fluid opening; and fluid outlet means extending from said housing in fluid communication with the interior of said housing external of said filter pouch.

4. The filter assembly of claim 3 wherein said flexible sheets of said housing and said frame members of said pouch are plastic, said sheets being sealed to only said frame members outwardly from said filter membrane.

5. The filter assembly of claim 3 wherein said membrane filter media comprises mixed cellulose esters reinforced with polyester mesh.

6. A filter assembly of a conventional size convenient for positioning on the arm of a patient, and for use in the filtering of intravenous fluids during the administration of such fluids comprising: a closed housing; a flexible filter pouch in said housing, said pouch formed from a porous membrane filter media having a pore size not greater than 0.22 microns, a porous support material overlying one surface of said filter media and a flexible frame member overlying the opposite surface of said filter media, said frame member having at least one opening exposing a substantial surface area of said filter media, said frame, support material and filter media all being folded substantially in half and being sealed along two edges adjacent the folded edge to form said pouch so that the edge of said pouch opposite said folded edge defines a fluid opening in said pouch, said folded pouch providing a sufficiently low pressure drop thereacross, so as to eliminate the requirement of a fluid pump to force said fluids through said assembly, fluid inlet means extending into said housing in fluid communication with the interior of said filter pouch through said fluid opening; and fluid outlet means extending from said housing in fluid communication with the interior of said housing external of said filter pouch; whereby, fluid may pass through said fluid inlet means into the interior of said filter pouch, pass through said opening of said frame, said filter media and said support material of said pouch into the interior of said housing external of said pouch and then exit from said house through said fluid outlet means.

7. The filter assembly of claim 6, wherein said support material is a polyvinylchloride scrim and said frame member is a film of polyvinylchloride.

8. A filter assembly of a conventional size convenient for positioning on the arm of a patient, and for use in the filtering of intravenous fluids during the administration of such fluids comprising: a substantially planar housing comprising a pair of flexible plastic sheets sealed together around their peripheries; a flexible filter pouch in said housing, said pouch formed from a porous polycarbonate film having a pore size not greater than 0.22 microns and a sheet of porous, flexible support material overyling at least one surface of said film, said support material and said film being folded substantially in half and being sealed together with said flexible sheets along two edges adjacent said folded edge, said pouch having a fluid opening in the end opposite said folded edge, said folded pouch providing a sufficiently low pressure drop thereacross, so as to eliminate the requirement of a fluid pump to force said fluid through said assembly; fluid inlet means extending into said housing in fluid communication with the interior of said filter pouch through said fluid opening; and fluid outlet means extending from said housing in fluid communication with the interior of said housing external of said filter pouch, whereby said flexible plastic sheets are adapted to be compressed together with said flexible filter pouch therebetween for facilitating the priming of the filter assembly to substantially eliminate any air space within said housing.

9. The filter assembly of claim 8, wherein said flexible pouch further includes a flexible frame member overlying the surface of said film opposite said supported surface, said frame member being sealed around its periphery to said film, said frame member having at least one opening exposing a substantial surface ara of said film, said frame member also being folded substantially in half to conform to said folded film and being sealed to said flexible sheets along said edges of said pouch, said flexible frame cooperating to provide a sufficient seal of said film of said housing sheets, but being sufficiently flexible to also facilitate in the priming of the filter assembly.

10. The filter assembly of claim 8, wherein said sheet of porous support material is a polyvinylchloride scrim.

* * * * *